United States Patent [19]

Love et al.

[11] Patent Number: 5,629,871
[45] Date of Patent: May 13, 1997

[54] WEAR TREND ANALYSIS TECHNIQUE FOR COMPONENTS OF A DIALYSIS MACHINE

[75] Inventors: Steve Love, Bailey; Jim Rosa, Conifer; Robert Chambers, Morrison, all of Colo.

[73] Assignee: Cobe Laboratories, Inc., Lakewood, Colo.

[21] Appl. No.: 486,942

[22] Filed: Jun. 7, 1995

[51] Int. Cl.⁶ .................................................. A61M 1/16
[52] U.S. Cl. ........................ 364/551.01; 210/646; 210/85
[58] Field of Search ........................... 364/551.01, 552, 364/557, 558, 571.01, 571.02, 571.07, 571.08, 579, 580, 413.02, 413.03, 413.07, 413.11, 183–186; 604/4, 1, 6, 65, 66, 67, 27–31; 210/646, 647, 85–95; 128/630, 691, 692

[56] References Cited

U.S. PATENT DOCUMENTS

| | | |
|---|---|---|
| 4,651,563 | 3/1987 | Zweifel . |
| 4,661,246 | 4/1987 | Ash ............................................ 210/87 |
| 4,954,974 | 9/1990 | Howell, IV et al. . |
| 5,053,815 | 10/1991 | Wendell . |
| 5,399,157 | 3/1995 | Goux et al. ................................. 604/4 |
| 5,401,238 | 3/1995 | Pirazzoli ..................................... 604/4 |
| 5,438,510 | 8/1995 | Bryant et al. ......................... 364/413.11 |
| 5,472,614 | 12/1995 | Rossi ....................................... 210/646 |
| 5,486,286 | 1/1996 | Peterson et al. ........................... 210/87 |

FOREIGN PATENT DOCUMENTS 0516534 of 0000 European Pat. Off. .

*Primary Examiner*—James P. Trammell
*Attorney, Agent, or Firm*—John R. Ley

[57] ABSTRACT

The wear on components in a dialysis machine is analyzed for the purpose of making repair and maintenance decisions. The actual performance of components is used to establish a test value. The test value is compared to a threshold value which represents the limits of normal performance of the component. Each instance where the test value exceeds the threshold value is counted and a maintenance count value is developed. The maintenance count value represents the number of abnormal performance events, and the maintenance count value is used to make maintenance and repair decisions. The test value developed for each component varies according to the type of component. The maintenance count values may be displayed for use by service personnel.

29 Claims, 9 Drawing Sheets

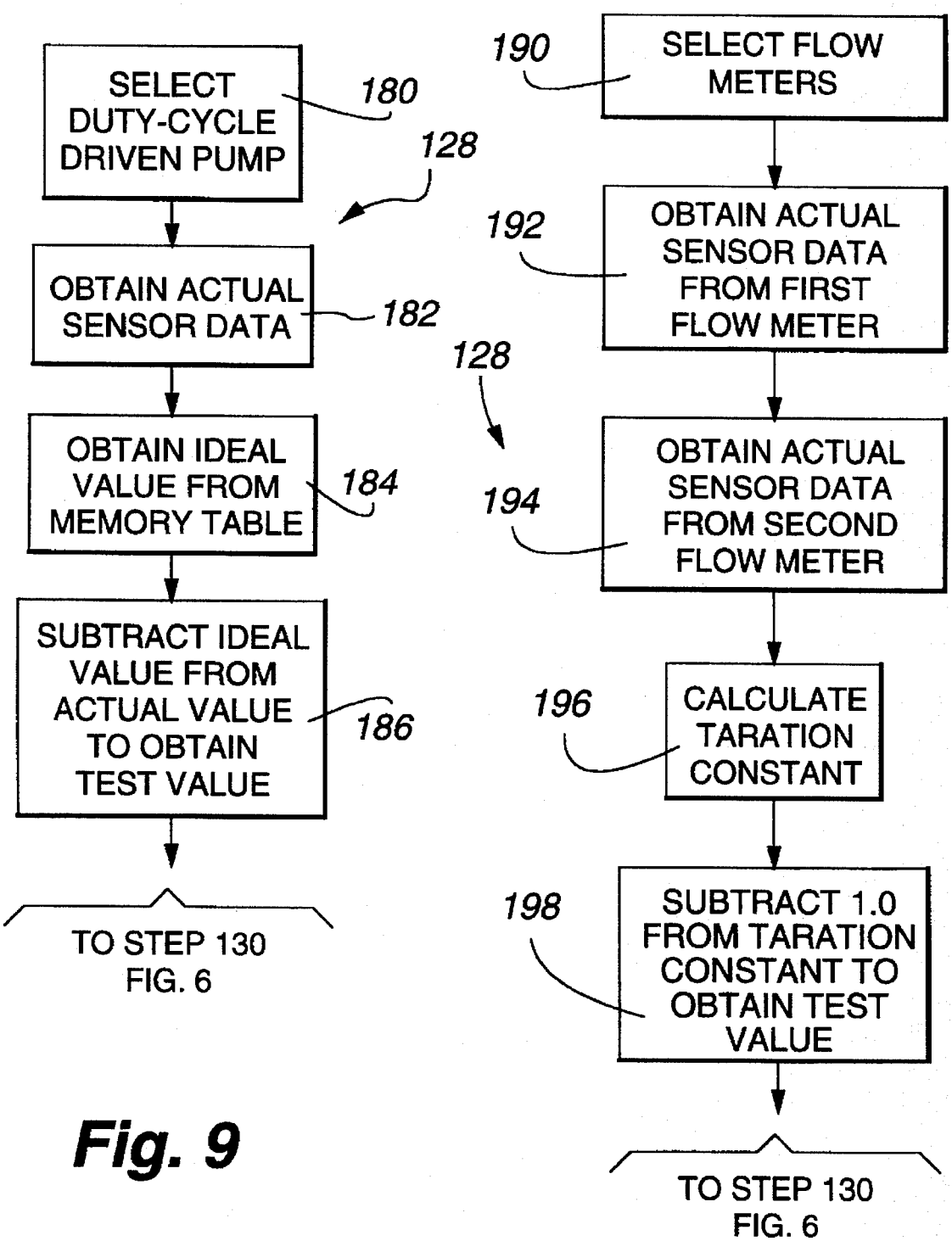

WEAR TREND ANALYSIS TECHNIQUE FOR COMPONENTS OF A DIALYSIS MACHINE

This invention relates generally to dialysis machines and more particularly, to a new and improved method and apparatus for performing trend analysis on components of the dialysis machine to identify those components which are likely to fail or malfunction due to wear and to make maintenance and service decisions with respect to those components.

BACKGROUND OF THE INVENTION

In general, a dialysis machine is used as a substitute for the natural kidney functions of a human body. As such, the dialysis machine cleans the blood of the natural accumulation of bodily wastes by separating the wastes from the blood outside the body or extracorporeally. The separated wastes are discharged and the cleansed blood is returned to the body.

A dialysis machine uses a dialyzer to separate the wastes from the blood. The dialyzer includes a porous medium located within an enclosure which separates the dialyzer into a blood compartment and a dialysate compartment. The blood removed from the patient flows through the blood compartment, and a prepared solution of dialysate flows through the dialysate compartment. The wastes from the blood pass through the medium by osmosis, ionic transfer or fluid transport into the dialysate, and depending upon the type of dialysis treatment, desirable components from the dialysate may pass in the opposite direction through the medium into the blood. The transfer of the wastes from the blood into the dialysate cleanses the blood while allowing the desired components from the dialysate to enter the bloodstream.

Accomplishing these functions requires a number of complex systems and components. In an extracorporeal flow path, which conducts blood from the patient to the dialyzer and then back to the patient, at least one arterial blood pump and sometimes a venous blood pump move the blood and assist in performing certain types of dialysis treatment such as ultrafiltration. A hydraulics flow path, which conducts the dialysate through the dialyzer, includes numerous components to monitor and control the conditions in that flow path. Flow meters are located at the inlet and outlet of the dialyzer. One dialysate pump moves dialysate into the dialyzer, and another dialysate pump removes the dialysate from the dialyzer. Sterilant pumps deliver a predetermined amount of disinfectant into the hydraulics flow path for disinfecting the hydraulics flow path prior to the treatment. An ultrafiltration pump is used in ultrafiltration dialysis treatments to control the delivery of desirable components to the blood. A heater heats the dialysate to body temperature to avoid undesirable heat transfer to or from the patient. The heater is also used to heat the disinfecting solution to temperatures adequate to kill microorganisms. Many other equally important components are required to function properly both during treatment and to prepare the machine for use.

In addition to the individual components, the dialysis machine usually includes a control system and a safety system. The control system controls the normal operation of these components during dialysis treatments and during the preparation of the machine for the treatment. The safety system monitors the performance of these components and the functionality of the control system. If the control system functionality or components fails, the safety system assumes control and places the dialysis machine in a safe state to avoid risks to the patient.

Since all of these components are subject to mechanical wear from use, the components occasionally fail and ultimately wear out. The typical practice is to conduct regular scheduled maintenance on dialysis machines, during which some components may be replaced prior to failure or malfunction. The replacement decisions are primarily at the discretion and judgment of the maintenance personnel. Components which are not replaced during regularly scheduled maintenance intervals usually fail during dialysis treatments.

Failure during a treatment generally does not place the patient in an unsafe position because of the safety features incorporated into the safety system. The patient may experience the inconvenience of the delay in treatment while another dialysis machine is substituted, and the clinic may experience the inconvenience of adjusting the treatment schedules of patients due to the delays in treatment, thereby decreasing efficiency. One significant inconvenience associated with an equipment failure is that a special maintenance service call is normally required. Special service calls are usually more costly than regularly scheduled service calls. Perhaps a more significant consequence of component failures is the downtime during which the dialysis machine is not available for treating patients.

The cost of dialysis treatments is in some measure related to the cost of upkeep of the dialysis equipment, and the ability to make maximum use of the dialysis equipment. With the public sentiment toward reducing or containing the costs of medical care, increased maintenance costs have a direct influence on the ultimate costs of medical treatment.

These and other problems, issues and concerns have given rise to the present invention.

SUMMARY OF THE INVENTION

An important feature of the present invention relates to monitoring parameters associated with the performance of components of the dialysis machine to obtain information useful in making decisions to replace or service those components. Another important feature is to obtain useful information concerning the performance of components in a dialysis machine by which to make service and replacement decisions. Another important feature is to obtain information concerning the components which is useful in predicting failures prior to an actual failure and in scheduling maintenance prior to such predicted failures. An important end result of the present invention is reduced costs of operating and maintaining dialysis machines.

In accordance with these and other features, the present invention is generally directed to a method of analyzing wear on components in a dialysis machine and to a dialysis machine which includes a safety and control system having a processor device using memory by which to develop the analysis information. The steps of the method and the functionality of the processor device and other components of the dialysis machine are generally concerned with establishing a threshold value which defines the limits of normal performance for each component to be analyzed, monitoring the actual performance of each component during use of the dialysis machine, determining a test value from the actual performance monitored and comparing the test value to the threshold value. Based on the comparison, a maintenance count value is incremented in relationship to each abnormal event when the test value exceeds the threshold value. The maintenance count value may be displayed or otherwise referenced to analyze the wear on the components.

The test values for each dialysis machine component are developed according to the type of component. For example, a test value for a pump which performs in a manner related directly to the value of voltage or current which energizes a motor that drives the pump will use the actual current or voltage value has the test value. A test value for a peristaltic pump may be determined by the actual stroke volumetric capacity. A test value for an ultrafiltration pump can be related to its actual feedback value calculated during the performance of an ultrafiltration dialysis treatment. A test value for the relative flow calibration of two flow meters may be based on a taration constant derived by a ratio of the actual indicated flow values measured by each flow meter. A test value for two gear or impeller pumps is derived from a ratio of the on time of the duty cycles that energize the motors while driving the pumps under equal pressure conditions. A test value for a duty cycle driven pump motor is determined by the actual on time of the duty cycle energizing the motor and an ideal value of the on time under the same ideal conditions.

Many other preferred aspects of the present invention, and a more complete appreciation of the present invention and its scope, may be understood from the accompanying drawings, which are briefly summarized below, from the following detailed description of a presently preferred embodiment of the invention, and from the appended claims.

BRIEF DESCRIPTION OF THE DRAWINGS

FIG. 9 is a flow chart illustrating the actions shown in FIG. 6 of computing a test value for a duty cycle driven pump in an extracorporeal flow path or a hydraulics flow path shown in FIGS. 3 and 4.

FIG. 10 is a flow chart illustrating the actions shown in FIG. 6 of computing a test value for two flow meters in a hydraulics flow path shown in FIGS. 3 and 4.

DETAILED DESCRIPTION

Figure 1:
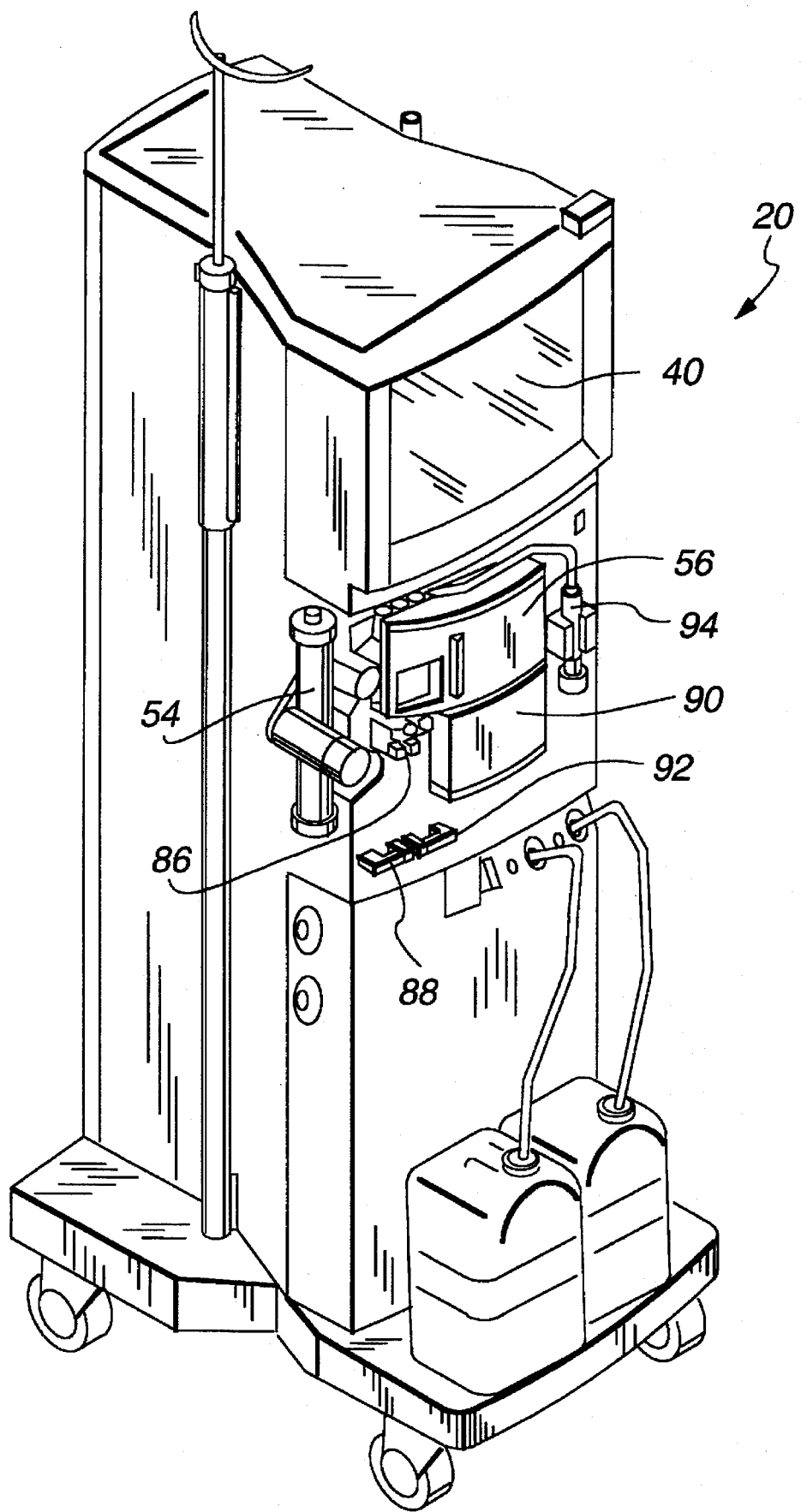
FIG. 1 is a perspective view of a dialysis machine which incorporates the present invention.
Figure 2:
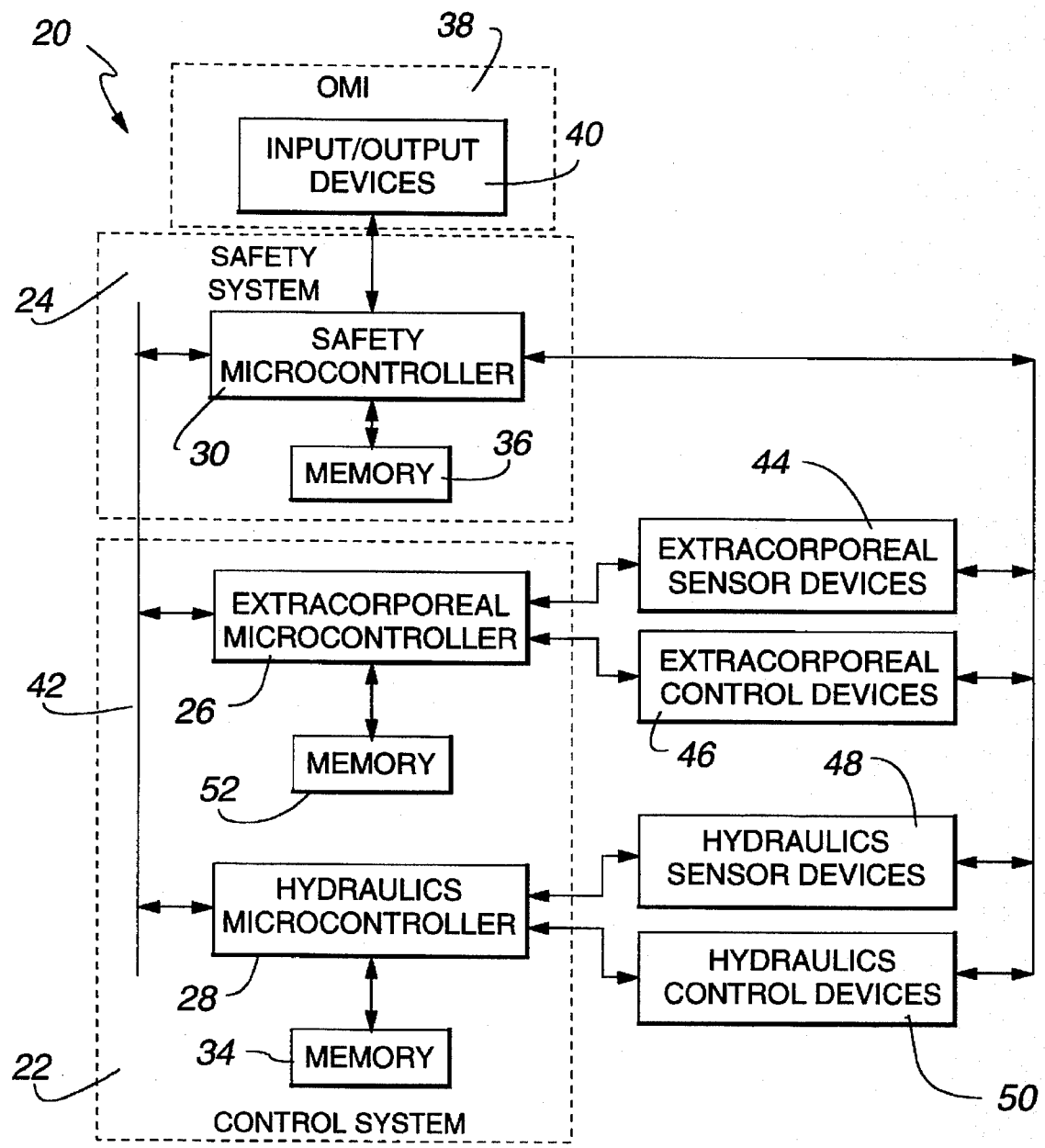
FIG. 2 is a block diagram of a control system and a safety system of a dialysis machine shown in FIG. 1.

The present invention is advantageously incorporated in a dialysis machine, such as that shown generally at 20 in FIGS. 1 and 2. The dialysis machine 20 is used to perform a variety of different and well-known dialysis treatments on a patient. To perform the dialysis treatments adequately and to protect the patient from risks during the treatment, the dialysis machine 20 includes a control system 22 and a safety system 24. The functions of the control system 22 are accomplished substantially by an extracorporeal microcontroller 26 and a hydraulics microcontroller 28. The functions of the safety system 24 are performed by a safety system microcontroller 30. Each microcontroller 26, 28 and 30 includes its own memory 32, 34 and 36, respectively, in which programs are recorded for controlling the microcontrollers and the components of the dialysis machine 20. Preferably the safety system memory 36 includes a nonvolatile or permanent portion to prevent the loss of functionality after recovering from an unexpected power failure.

Control and safety information is supplied to the dialysis machine through an operator/machine interface (OMI) 38. The OMI 38 includes an input/output (I/O) device 40 through which the entered information is supplied to the protective microcontroller 30 and from which operating and safety information is displayed to the operator. The OMI 38 may also include its own processor for assisting in the input and output of information. Information is directly transferred and shared between the microcontrollers 26, 28 and 30 over a bus or network 42.

Figure 3:
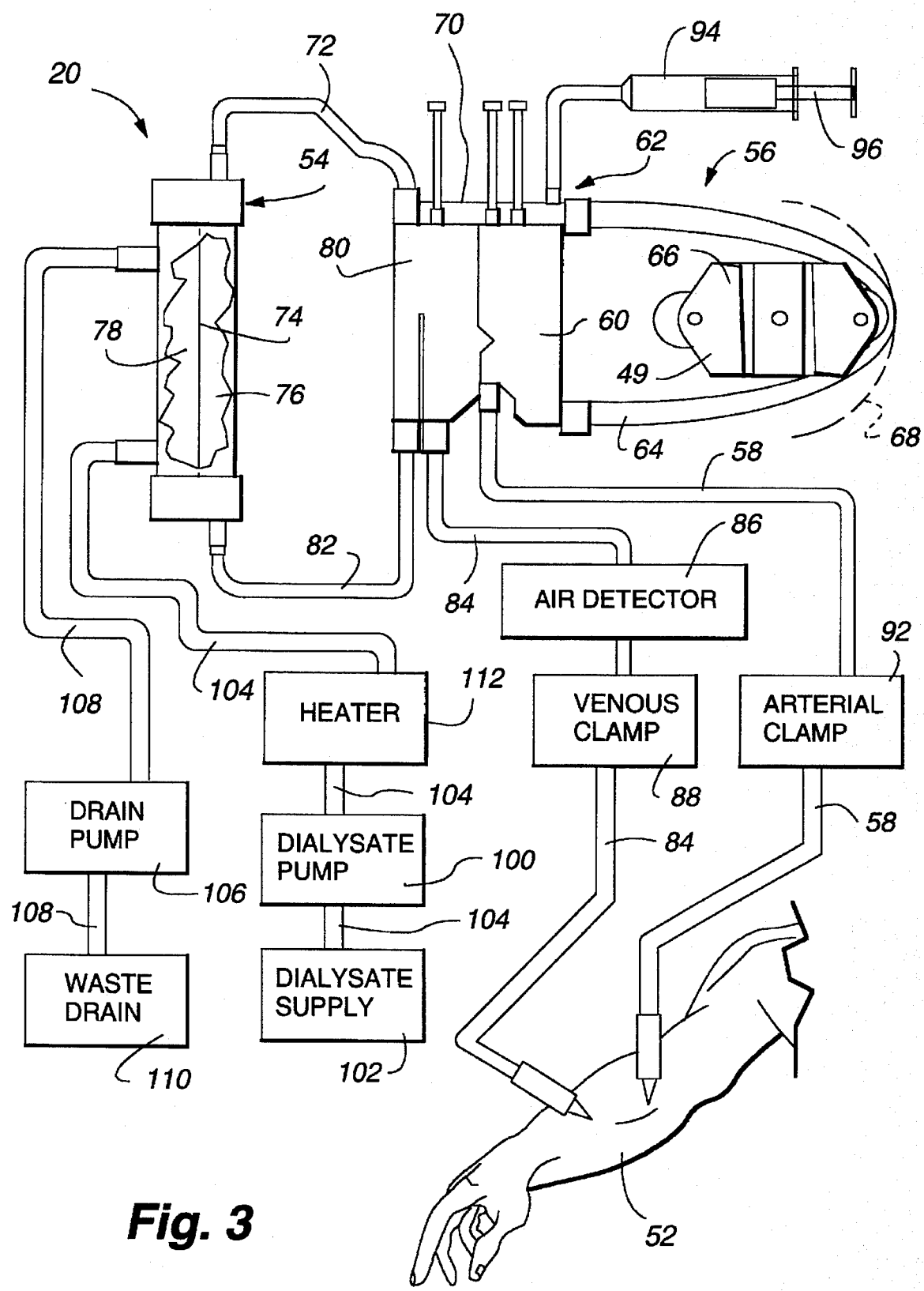
FIG. 3 is a generalized view illustrating some of the typical components of an extracorporeal flow path and a hydraulics flow path of the dialysis machine shown in FIGS. 1 and 2.
Figure 4:
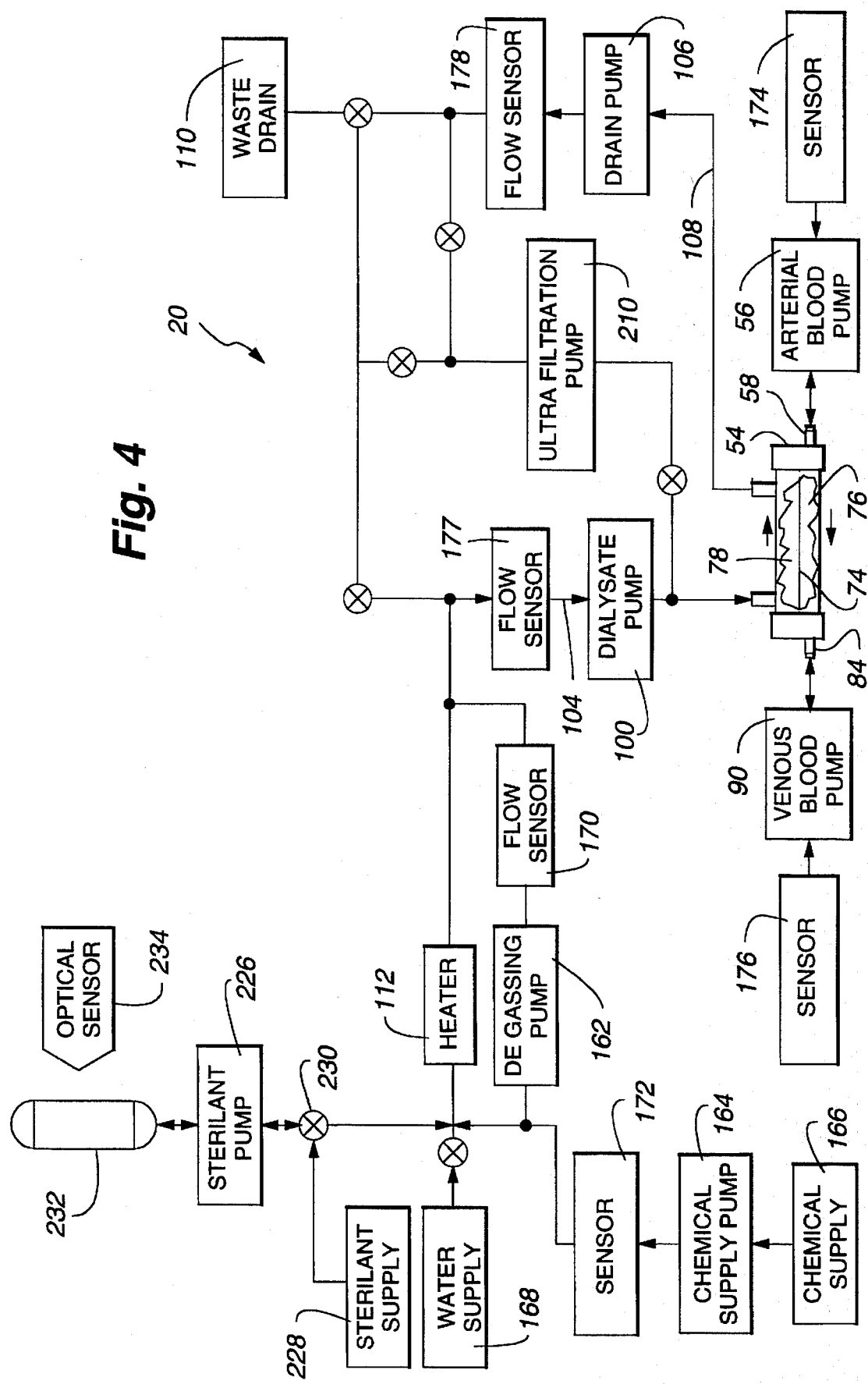
FIG. 4 is a more detailed diagram of more of the components of the hydraulics and extracorporeal flow paths shown in FIG. 3.

The components of the dialysis machine 20 establish an extracorporeal flow path and a hydraulics flow path, which are shown in FIGS. 3 and 4. Blood from the patient flows through the extracorporeal flow path where it is cleansed and then returned to the patient. Dialysate flows through the hydraulics flow path to remove the wastes transferred to the dialysate. The extracorporeal flow path includes sensors 44 and control devices 46 to sense blood flow conditions and control the blood flow. Similarly the hydraulics flow path also includes sensors 48 and control devices 50 to sense conditions of the dialysate and control its characteristics.

The sensors 44 and 48 and the control devices 46 and 50 in the extracorporeal and the hydraulics flow paths are connected to the microcontrollers of both the control system 22 and the safety system 24. Should either the control system 22 or the safety system 24 experience a malfunction, the other system can assume control over the dialysis machine 20 and place it in a safe patient state where the risk to the patient is eliminated or minimized.

More details concerning the extracorporeal flow path are shown in FIGS. 3 and 4. Blood flows from a patient 52 through a conventional dialyzer 54 and back to the patient 52. An arterial blood pump 56 (usually peristaltic, as shown) draws blood from the patient 52 through an arterial line 58 and into an arterial chamber 60 of a blood handling cartridge 62. The blood pump 56 draws blood from the arterial chamber 60 through a pump tubing 64 which is squeezed or pinched by a rotating rotor 66 against a stationary raceway 68. The blood within the pump tubing 64 is propelled into a manifold 70 of the blood handling cartridge 62 and then through a tube 72 and into a blood inlet of the dialyzer 54.

A micro-porous or other type of dialysis medium 74 divides the interior of the dialyzer 54 into a blood chamber 76 and a dialysate chamber 78. While in the dialyzer 54, the waste products from the patient 52 are separated from the blood, and the cleansed blood is transferred back to a venous chamber 80 of the cartridge 62 through a tube 82. Any unintentionally introduced air in the blood is extracted while in the venous chamber 80.

After leaving the venous chamber 80 the blood flows through a venous line 84 to an air detector 86. The air detector 86 derives signals related to the quantity of air, if any, remaining in the venous line 84. If an excessive amount of air is present, a protective control signal will be generated and a venous line clamp 88 will immediately close to terminate the flow of blood through the venous line 84 before the air reaches the patient 52. In some types of dialysis treatments a venous blood pump 90 (FIG. 4) is located in the venous line 84 to assist in returning the blood to the patient 52. An arterial clamp 92 is located in the arterial line 58 for the purpose of stopping the flow of blood in the arterial line 58 when necessary or desired.

Because the blood in the extracorporeal flow path is prone to clot, an anticoagulant such as heparin is injected into the extracorporeal flow path. The anticoagulant is slowly delivered from a syringe 94. A plunger 96 is displaced into the syringe 94 by a driver mechanism (not shown). The driver mechanism and the syringe 94 are typically referred to as a heparin pump or an anticoagulant pump.

The components of the hydraulics flow path are also shown in greater detail in FIGS. 3 and 4. The hydraulics flow path includes a dialysate pump 100 which draws dialysate from a supply 102. The supply 102 of dialysate is prepared by the dialysis machine from purified water and a supply of chemicals, or is obtained from an external source of previously prepared dialysate. The dialysate pump 100 delivers the dialysate through a dialysate supply line 104 to the dialysate chamber 64 of the dialyzer 54. The dialysate flows past the medium 74 where it absorbs the waste products transferred from the blood in the blood chamber 76. Any beneficial components in the dialysate which are to be transferred into the blood pass through the medium 74 and into the blood in the blood chamber 76.

Dialysate containing the waste products is removed from the dialysate chamber 78 by a drain pump 106 which is connected to the dialyzer 54 by a dialysate drain line 108. The used dialysate in the dialysate drain line 108 is delivered to a waste drain 110. The waste drain 110 may be a separate container or a connection to a public sewer.

A heater 112 is located in the dialysate supply line 104. The heater 112 raises the temperature of the dialysate supplied to the dialyzer 54 to a temperature commensurate with the body temperature of the patient 52. Heat transfer between the blood and the dialysate in the dialyzer 54 is avoided in this manner to prevent thermal distress in the patient. The heater 112 also functions during disinfection of the hydraulics flow path. During disinfection, any microorganisms which might be found in the hydraulics flow path are destroyed. A solution of sterilant, which is formed from disinfecting chemicals, is directed through the hydraulics flow path. Frequently the sterilant will also be heated to aid in destroying the microorganisms. The heater 112 is employed to heat the sterilant under disinfecting conditions.

In addition to the elements just described, the hydraulics flow path also includes a number of flow control valves (many of which are not shown), and a number of sensors (many of which are not shown) for determining characteristics of the dialysate, such as conductivity sensors, pH sensors, temperature sensors and others, all of which are generally known in the field of dialysis machines.

The hydraulics flow path contains many of the components which are subject to the trend analysis. More details concerning the functionality of those components are discussed below specifically with regard to their characteristics which make them susceptible to trend analysis.

In general, the trend analysis technique of the invention involves monitoring a characteristic operating parameter of a component of the dialysis machine and comparing the monitored characteristic to a threshold value. Should the monitored characteristic deviate from the threshold value, an abnormal event will be recognized. The occurrence of the abnormal event will increment a maintenance counter. The maintenance counter will record information relating to each abnormal event occurring during use of the dialysis machine. The information from the maintenance counter is analyzed to make decisions concerning the replacement or service of the component subject to the trend analysis. The threshold value is generally a value representing the level or range of acceptable performance of the component. The threshold value is established by the operator or the manufacturer of the dialysis equipment for determining whether the monitored characteristic operating parameter of the component represents an unacceptable deviation from the normal characteristics.

Predictions of component failure are obtained by calculating or observing a trend value related to the change in the maintenance count value relative to another parameter such as time. The trend will be evaluated as a basis to predict or estimate the failure of the component and to estimate a date or time for replacing that component. Such predictions can also be employed to generate an alarm to alert the maintenance personnel of the necessity to replace the component.

The basic features of the invention are shown in FIGS. 5-8. Specific features involved in certain basic features are shown in FIGS. 9-14. Some of the activities involved in the invention are actions that are taken or that may be taken by the maintenance personnel for the dialysis machine, and some of the actions are or may be performed by the control system and safety system of the dialysis machine. Aspects of the invention are shown as steps in the flow charts of FIGS. 5-8, and each of the steps is separately designated by a reference numeral for convenience of description.

Figures 5, 6:
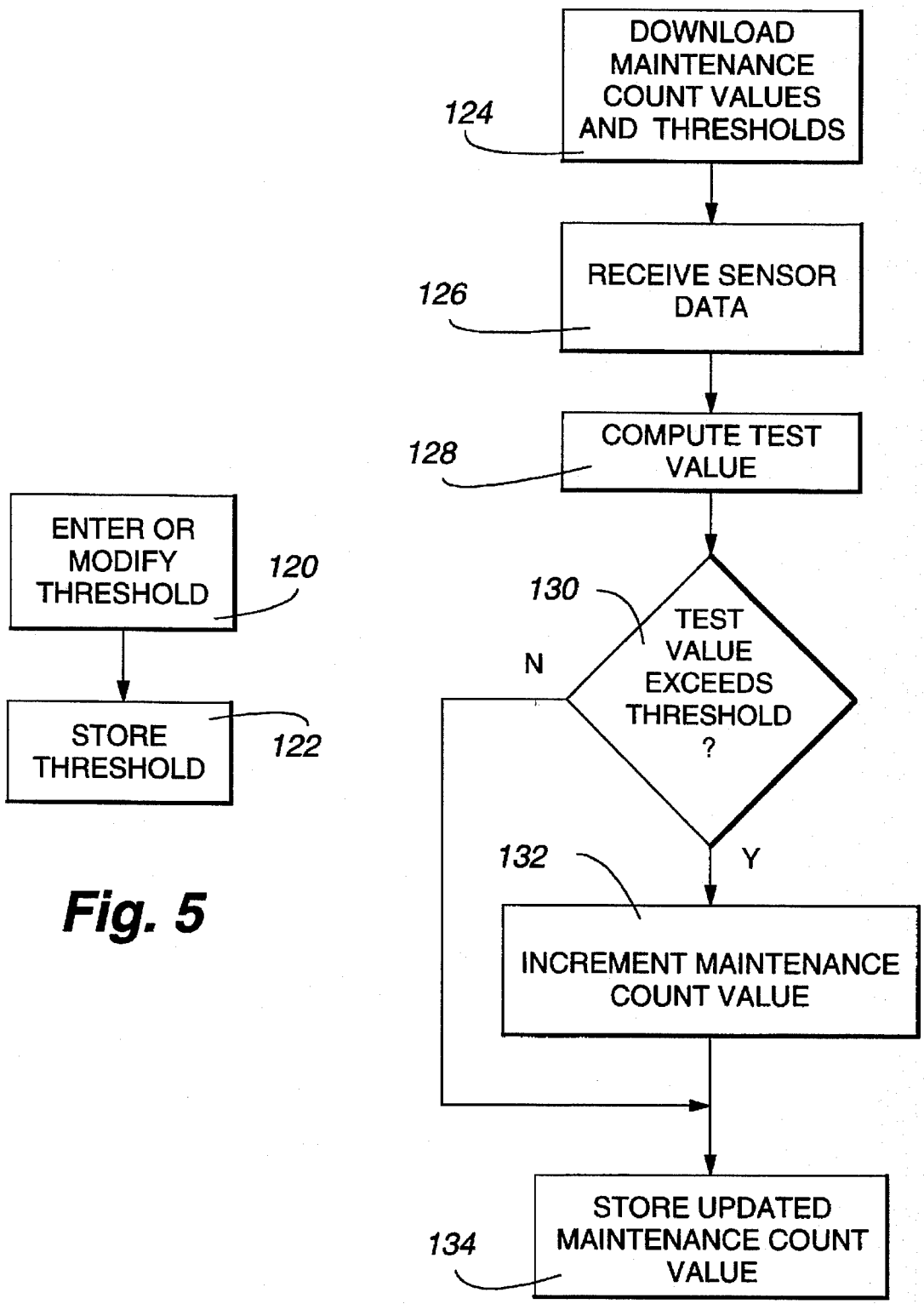
FIG. 5 is a flow chart illustrating actions involved in establishing or modifying a threshold to evaluate the condition of the components which are subject to the trend analysis of the present invention.
FIG. 6 is a flow chart illustrating actions involved in detecting events that describe the condition of the components which are subject to the trend analysis according to the present invention.

The basic feature of entering or modifying the threshold value which represents the level of normal performance of the component is shown in FIG. 5. At step 120, the operator enters or updates the thresholds for each component to be subject to the trend analysis. For example, the normal limits of a duty cycle for driving a pump motor may be selected by the operator, suggested by the pump manufacturer, or established by the manufacturer of the dialysis machine. Should the duty cycle necessary to drive the pump motor exceed or fall outside of the upper or lower limit which constitutes the threshold, an abnormal event would result and indicate a circumstance or situation of unusual or abnormal performance. Thus, each threshold represents the tolerance limit or range of normal operation of the component subject to trend analysis.

The threshold value entered at 120 is stored into memory, preferably permanent memory, at 122. The permanent memory is part of the memory 36 (FIG. 2) connected to the protective microcontroller 30. Storing the threshold values in nonvolatile memory protects them against loss or destruction from unanticipated power outages and other malfunctions. The threshold values are therefore available over extended periods of time.

The basic features shown in FIG. 6 involve detection of abnormal events which indicate operation of the component beyond the threshold. The sequence of events shown in FIG. 6 occurs during each operation of the dialysis machine. At 124, the threshold value of each component under analysis is downloaded or transferred from the protective memory 36 (FIG. 2) to the extracorporeal microcontroller 26 and/or the hydraulics microcontroller 28 over the network 42. During operation of the dialysis machine, information or data from the extracorporeal sensor devices 44 (FIG. 2) and the hydraulics sensor devices 48 is supplied at 126 to the microcontrollers 26 and 28. The sensor data is available for each of the components analyzed.

A test value is computed or calculated at step 128 by using the sensor data supplied at 126 or the commanded values of a parameter supplied to the component (e.g. the duty cycle of energizing power supplied to a stepper motor) and the threshold value obtained at 124. The test value is that value which represents the operating circumstances of each component under the specific conditions. In some circumstances described below, the test value computed at 128 will be the data received from the sensors at 126. In other cases described below, the test value at 128 will result from a mathematical calculation performed using the sensor data received at 126. Consequently, the test value generally must be calculated for each component depending upon its actual operating conditions. The steps for calculating the test values for a number of different components which will normally be subject to trend analysis in a dialysis machine are shown and separately described in conjunction with FIGS. 9–14.

A comparison of the test value calculated at 128 to the threshold value is performed at 130. If the comparison at 130 reveals that the test value exceeds or falls outside of the limits of the threshold, an abnormal event has occurred and a maintenance count value is incremented at 132. The maintenance count value is a value recorded in the memory which represents the total number of abnormal events that have occurred when the operating conditions of the component under analysis exceeded the threshold or normal operating tolerances. For prediction purposes, the time and date of each abnormal event are also preferably recorded along with the fact of the occurrence of such abnormal event. If the comparison at 130 reveals that the test value is not uniquely different from the threshold, the maintenance count value is not incremented. After each incrementation of the maintenance count value at 132 or after each determination at 130 that the test value is not uniquely different from the threshold, the maintenance count value is recorded in memory, as shown at 134. The maintenance count value in memory is updated by transferring the information over the network 42 (FIG. 2).

Figures 7, 8:
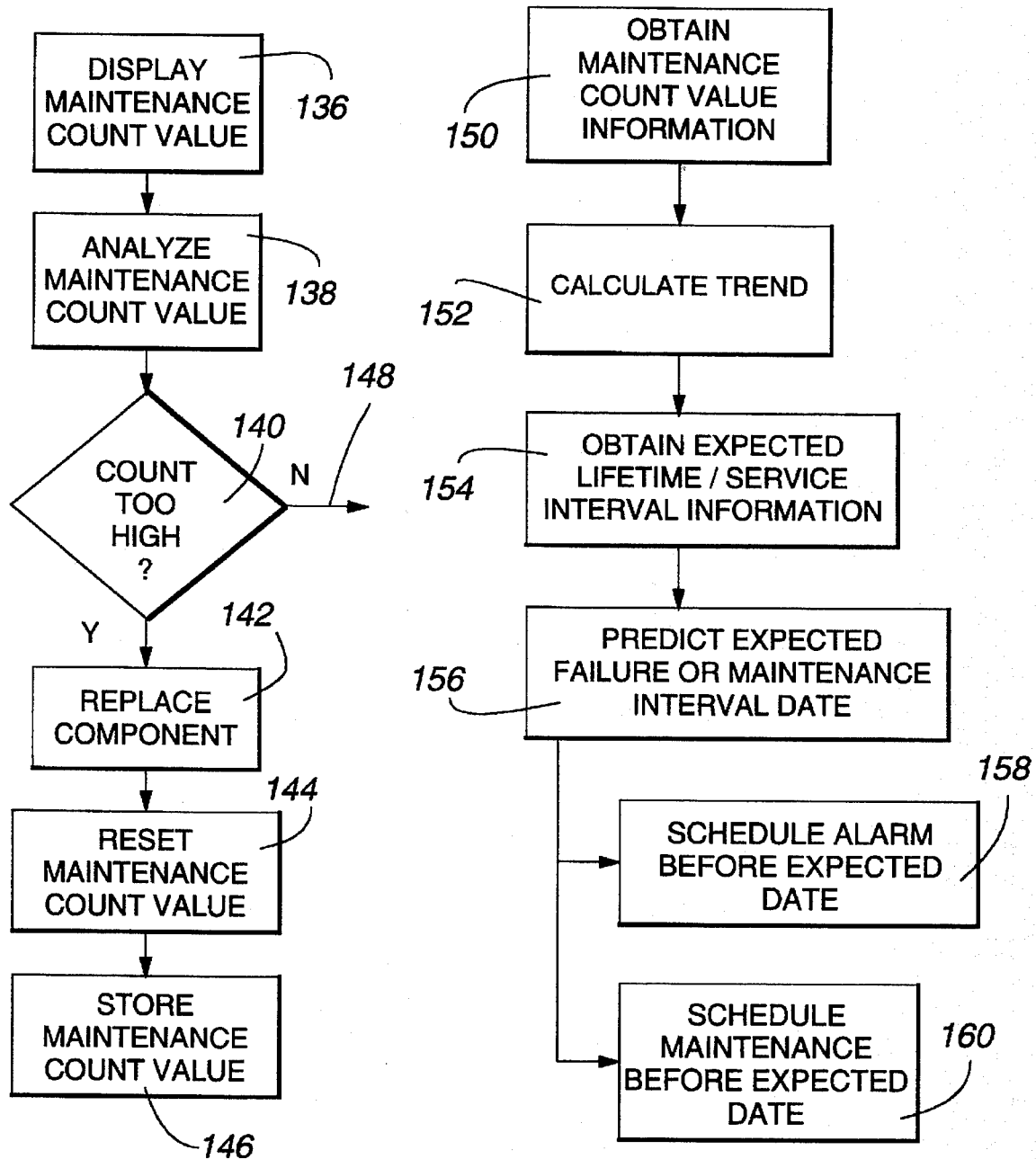
FIG. 7 is a flow chart illustrating actions involved in analyzing the condition of the components which are subject to trend analysis according to the present invention.
FIG. 8 is a flow chart illustrating actions involved in predicting the failure or malfunction of the components which are subject to trend analysis according to the present invention.

The basic features of the invention which relate to analyzing each component are illustrated in FIG. 7. At 136, the operator requests a display or other presentation of the maintenance count value for a selected one or more of the components. The display is accessed through the OMI I/O devices 40 (FIG. 2) which are connected to the protective microcontroller 30 to receive the maintenance count value from memory.

After obtaining the information requested at 136 the operator analyzes the maintenance count value at 138. The analysis performed at step 138 may be as simple as recognizing an excessive maintenance count value. More complex types of analysis may involve extrapolating the count value and dates associated with the abnormal events to predict a date of failure. The operator may schedule preventive maintenance based on the predicted date of failure, or take other actions based on the experience and judgment. The control and safety system microcontrollers 26, 28 or 30 (FIG. 2) may perform the analysis or the operator or a service technician may perform the analysis to analyze the condition of the component.

An example of the type of analysis action which the operator may take is shown by the steps 140, 142, 144 and 146. If the maintenance count is too high, as determined at 140, the operator may replace the component as shown at 142. Thereafter the operator resets the maintenance count value for the replaced component, as shown at 144. The reset maintenance count value is thereafter stored in memory as shown at 146. If the maintenance count value is not too high as determined at 140, the maintenance count value is left unmodified and the normal operation of the machine proceeds from the outcome 148 of the determination at 140. The actions of requesting the maintenance count value at 136, resetting the maintenance count value at 144 and storing the reset maintenance count value back to the memory is accomplished by the operator using the I/O devices 40 (FIG. 2).

The basic features involved in predicting component failure or replacement and scheduling maintenance before the anticipated date of failure are shown in FIG. 8. The steps shown may be performed entirely by the functionality of the control and safety system microcontrollers, or the steps may be performed manually, or the information may be downloaded from the dialysis machine and the steps performed by a separate computer. A combination of manual and automatically executed steps may also be employed. The maintenance count value information is first obtained at 150. The maintenance count value information includes the count value, and in this case, the dates associated with each abnormal event which gave rise to an increase in the maintenance count value. From this information, a trend in the occurrence of abnormal events is calculated at 152. The trend may project the rate of abnormal events forward in time.

Next, the expected lifetime or maintenance interval information for the individual component under consideration is obtained, as shown at 154. The expected lifetime or maintenance interval information may be supplied in memory with the dialysis machine, or may be entered or updated by the operator based on the experience of the operator with maintenance of the dialysis machine, or may be stored elsewhere on a different computer or in a different source of information. The expected lifetime or maintenance interval information is employed in a calculation or other extrapolation based on the trend obtained at 152. Based on experience, empirical information or estimates and the count value, trend and expected lifetime or service intervals, the projected lifetime or service interval may be projected.

Based on the expected failure or maintenance interval date predicted at 156, an alarm is scheduled at 158 to be delivered before the expected failure date or maintenance interval date. The alarm at 158 may be scheduled automatically by the control and safety system microcontrollers, in which case the alarm will also be delivered automatically based on the scheduled date, as calculated by the normal system clock maintained by the microcontroller. Otherwise, the operator manually schedules the alarm date.

Maintenance may also be scheduled at the same time as the alarm is scheduled at 158, or at a different earlier time from the alarm or expected failure or maintenance interval date determined at 156. By predicting failure or maintenance interval dates, a number of components having failure or maintenance interval dates occurring at comparable times may be serviced or replaced at the same time, thereby reducing the number of service calls. Scheduling the maintenance is shown at 160. Again, the system microcontrollers may schedule the dates for the maintenance or the scheduling might be done manually by the operator.

The trend analysis information can be accessed by a maintenance person during regularly scheduled maintenance events when the machine is not used in treatments, or the information can be accessed to evaluate the condition of the dialysis machine. In addition, the trend analysis information may be downloaded from the dialysis machine to a central maintenance computer or station and evaluated there.

There are a number of pumps in the dialysis machine which are advantageously subjected to the trend analysis of the present invention. Many of these pumps are driven by an electric stepper motor which is energized on a duty cycle basis. The on time of the duty cycle represents the amount of electrical power necessary to drive the motor. As the motor wears and as the pump which is driven by the motor wears, the amount of electrical power to achieve the desired performance is increased to compensate for the wear. Since most of the components of the dialysis machine include sensors (44 and 46, FIG. 2) to measure the performance of the component, and the extracorporeal and hydraulics microcontrollers (26 and 28, FIG. 2) utilize the sensor information to control the pumps and thereby achieve the desired flow rates, the on time of the duty cycle is readily adjustable to overcome the effects of wear. By monitoring the on time of the duty cycle and comparing that on time to the expected on time for a normally operating pump, the degree or extent of wear is readily determinable.

Examples of pumps in the dialysis machine which may be driven by a stepper motor energized on a duty cycle basis are the arterial blood pump 56, the venous blood pump 90 or infusate pump, the dialysate flow pump 100, the drain flow pump 106, a degassing pump 162, and one or more chemical supply pumps 164, all shown in FIG. 4. Usually a dialysis machine employs two chemical supply pumps 164, but only one is shown in FIG. 4. One chemical supply pump usually supplies bicarbonate from a chemical supply 166. The other chemical supply pump typically supplies acid from a separate chemical supply. The bicarbonate, acid or other chemical is mixed with water from a supply 168 to form the dialysate. Each chemical supply pump 164 is required to deliver precise quantities of the chemical to be mixed with the water and thereby achieve the desired composition of the dialysate. All of the components shown in FIG. 4 which are employed to prepare the dialysate are generally shown in FIG. 3 at 102.

The duty cycle driven flow pumps 100 and 106 and the degassing pump 162 have associated with them a flow sensor to measure their performance. A flow sensor 170 is located in the flow path where the degassing pump 162 circulates fluid around the heater 112. Flow sensors 174 and 176 are located in the dialysate supply line 104 and the dialysate drain line 108 to monitor the volumetric flow rates of the dialysate flow pumps 100 and 106.

A sensor 172 is associated with the chemical supply pump 164 to measure its rotational rate and to thereby determine the volumetric flow conducted by that pump 164. Sensors 174 and 176 are associated with the arterial blood pump 56 and venous blood pump 90 to measure the rotational rate of those pumps 56 and 90. From the rotational rates, the volumetric flow rate of the blood in the arterial line 58 and the venous line 84 is determined. The sensors 170, 174 and 176 are typically hall sensors which sense the movement of the rotors of the pumps with which may are associated. The sensors 170, 172, 174, 176, 177 and 178 are included in the extracorporeal and hydraulic sensor devices 44 and 48 shown in FIG. 2.

The computation 128 of the test value for one of the duty cycle driven pumps is shown in greater detail in FIG. 9. The duty cycle driven pump is selected at 180, and the data from the sensor associated with the blood pump is obtained at 182. The actual sensor data obtained at 182 is that data which represents the actual operating performance of the duty cycle driven pump.

The percentage of the on or conductive time in each duty cycle which drives the pump is monitored relative to the performance of the pump under the specific operating conditions. The specific operating conditions take into account the flow of fluid, the pressure of the fluid at the location of the pump, and other variables which influence the performance of the pump under those circumstances. The ideal value of the duty cycle on time for driving the pump under those same circumstances is recorded in a table in memory. The ideal value is obtained from the memory table at 184.

The test value is computed as the difference between the ideal value obtained at 184 and the actual value obtained from the sensor data at 182. This difference, which is determined at 186, becomes the test value. The test value therefore represents the difference between the actual operating value and the value which results from ideal conditions.

Even under the normal circumstances represented by the threshold established (step 120, FIG. 5), there will be an acceptable range of variability from one duty cycle driven pump to another such pump. Consequently, the threshold established for a duty cycle driven pump will be a range of acceptable deviation.

The test value obtained at 186 (FIG. 9) is compared with the range of acceptable deviations represented by the threshold at 130 in FIG. 6. Test values which exceed (fall outside of) the threshold range indicate the occurrence of an abnormal event which increments the maintenance count value at 132 (FIG. 6).

The computation 128 of the test value for the flow sensors or meters 177 and 178 (FIG. 4) in the hydraulics flow path is shown in greater detail in FIG. 10. The selection of the flow meters for consideration is shown at 190. The actual sensor data obtained from the two flow meters is obtained at steps 192 and 194. The actual sensor data obtained at 192 and 194 is used to calculate a ratio of the two values known as a taration constant, as shown at 196. The taration constant establishes a normalized tare value for comparing the relative performance of both flow meters 177 and 178. Under ideal testing conditions, the flow through each flow meter should be equal, and the resulting taration constant will be 1.0.

After calculation of the taration constant at 196, the hydraulics microcontroller subtracts the value of 1.0 from the taration constant, as shown at 198. The result of this subtraction is the test value, and the program flow thereafter continues at step 130 (FIG. 6).

In the case of the flow meters 177 and 178, the threshold established at 124 will constitute a normal range of deviation which is considered acceptable. Variations in the test value calculated at 198 which exceed (fall outside of) the threshold will be considered abnormal and will result in the incrementation of the maintenance count value, as shown at 130 and 132 in FIG. 6.

Generally variations in the flow measured through each flow meter will result from a buildup of dialysate chemicals within an interior flow passageway through those flow meters. The trend analysis information available from this invention may indicate that the flow meters should be cleaned of this buildup. The trend analysis information available concerning the flow meters may also be employed to recognize malfunctions or errors in the sensors which measure the flow through the flow meters.

Figures 11, 12:
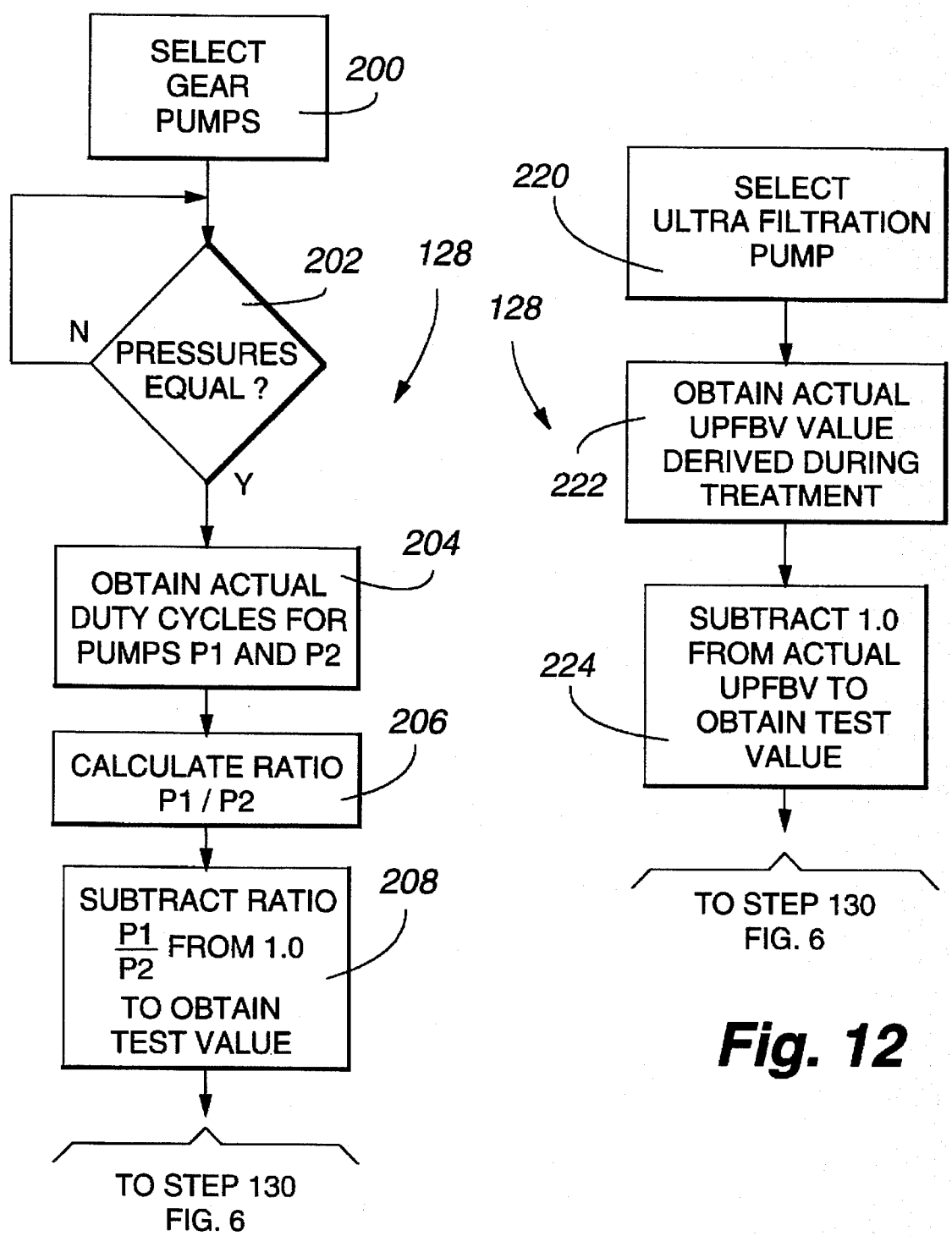
FIG. 11 is a flow chart illustrating the actions shown in FIG. 6 of computing a test value for gear pumps in a hydraulics flow path shown in FIGS. 3 and 4.
FIG. 12 is a flow chart illustrating the actions shown in FIG. 6 of computing a test value for a pump ultrafiltration feedback value in a hydraulics flow path shown in FIGS. 3 and 4.

The computation 128 of the test value for the performance of the flow pumps 100 and 106 (FIGS. 3 and 4) apart from the electrical motors which drive those pumps, is shown in greater detail in FIG. 11. These electrical motors are duty cycle driven, as described above. However, the flow producing components of these pumps are usually gears or impellers. The gears or impellers are also subject to wear, and the test value computed in FIG. 11 is an effective means for determining the condition of those gears or impellers.

The selection of the gear pumps or impeller pumps for trend analysis is shown at 200. In order to accurately evaluate the performance of these dialysate gear pumps 100 and 106, the hydraulic pressure on both pumps must be equal. The performance of gear or impeller pumps is pressure dependent, so an unequal pressure will prevent an accurate evaluation of the pumps. The step at 202 allows the computation of the test value to occur only when the pressures on both pumps are made equal. With both gear pumps experiencing the same pressure, they are operated at the same rpm, and the on time of the energizing duty cycle for each pump is obtained at 204. The two duty cycle values obtained at 204 are then divided to obtain a ratio as shown at 206. A unity ratio indicates that both gear pumps are operating similarly. The greater the deviation of the ratio from unity indicates a greater disparity in pump operation.

The ratio obtained at 206 is subtracted from unity at step 208, and the result is the test value. Since the ratio established at 206 is the ratio of the first pump duty cycle (P1) to the second pump duty cycle (P2), the test value obtained at 208 indicates both proper operation and which one of the two pumps is failing. A zero test value indicates that both pumps are operating adequately. A negative test value indicates that the second pump (P2) is failing because the ratio calculated at 206 is a value greater than 1.0. A positive test value indicates that the first pump (P1) is failing because the ratio calculated at 206 is a value less than 1.0.

The test value obtained at 208 is employed at step 130 in the flow shown in FIG. 6. The threshold established at 120 (FIG. 5) represents an acceptable range of variability in the relative performance of the two gear pumps. Consequently, the threshold downloaded at 124 (FIG. 6) will be a range of deviations with which the test value obtained at 208 (FIG. 11) is compared at 130. Test values falling outside of the range of the threshold indicate the occurrence of an abnormal event which increments the maintenance count value at 132 (FIG. 6).

The computation 128 of a test value for an ultrafiltration pump feedback value (UPFBV) by which to evaluate the condition of an ultrafiltration pump 210 (FIG. 4) is shown in greater detail in FIG. 12. Ultrafiltration is typically a part of a dialysis treatment in which fluid components from the blood are drawn through the medium 74 and into the dialysate, as is understood from FIGS. 3 and 4. The typical method of obtaining ultrafiltration is to create a different flow out of the dialysate outlet of the dialyzer 54 compared to the dialysate flow into the inlet of the dialyzer.

The ultrafiltration pump 210, shown in FIG. 4, is employed during ultrafiltration to create the differential in dialysate flows into and out of the dialyzer 54. The ultrafiltration pump 210 is connected between the dialysate supply line 108 and the dialysate drain line 110. Operation of the ultrafiltration pump 210 increases or decreases the flow of dialysate out of the dialyzer at the outlet of the dialyzer. The ultrafiltration pump 210 is employed because it is usually the case that both flow pumps 100 and 106 are operated at the same rate. The operation of the ultrafiltration pump 210 establishes the rate of ultrafiltration independently of the rates of operation of the dialysate supply and drain pumps.

During a typical automatic calibration procedure of the dialysis machine, the ultrafiltration pump 210 is operated while the dialysate supply and drain pumps 100 and 106 also operate. The flow rates are measured by the sensors 177 and 178 until the flow rates are equal. The value of the control signal to the ultrafiltration pump 210 is determined under this condition and that value is established as a unity (1.0) UPFBV. During the ultrafiltration dialysis treatment the UPFBV is adjusted to achieve the desired accuracy of ultrafiltration. This adjusted rate is then employed to evaluate the performance of the ultrafiltration pump after the conclusion of the treatment.

The computation of the test value 128 for the UPFBV is shown in greater detail in FIG. 12. The ultrafiltration pump is selected for analysis at 220. The actual UPFBV value which resulted from the adjustment during the previous ultrafiltration treatment is obtained at 222, by reading the UPFBV value from memory. The actual UPFBV value obtained at 222 is subtracted from unity (1.0) and the result is the test value, as shown at 224. After calculation of the test value at 224, the program flow continues at step 130 shown in FIG. 6.

The UPFBV threshold established at 120 (FIG. 5) will constitute a normal range of deviation which is considered acceptable operation for the ultrafiltration pump. Variations in the test value calculated at 224 (FIG. 12) beyond the threshold obtained at 124 (FIG. 6) will be considered as abnormal events which will increment the maintenance count value at 132 (FIG. 6). Instances where the maintenance count value for the UPFBV is incremented are those which may arise do to control malfunctions in the ultrafiltration pump 210 as well as malfunctions in the pump 210 itself.

Figures 13, 14:
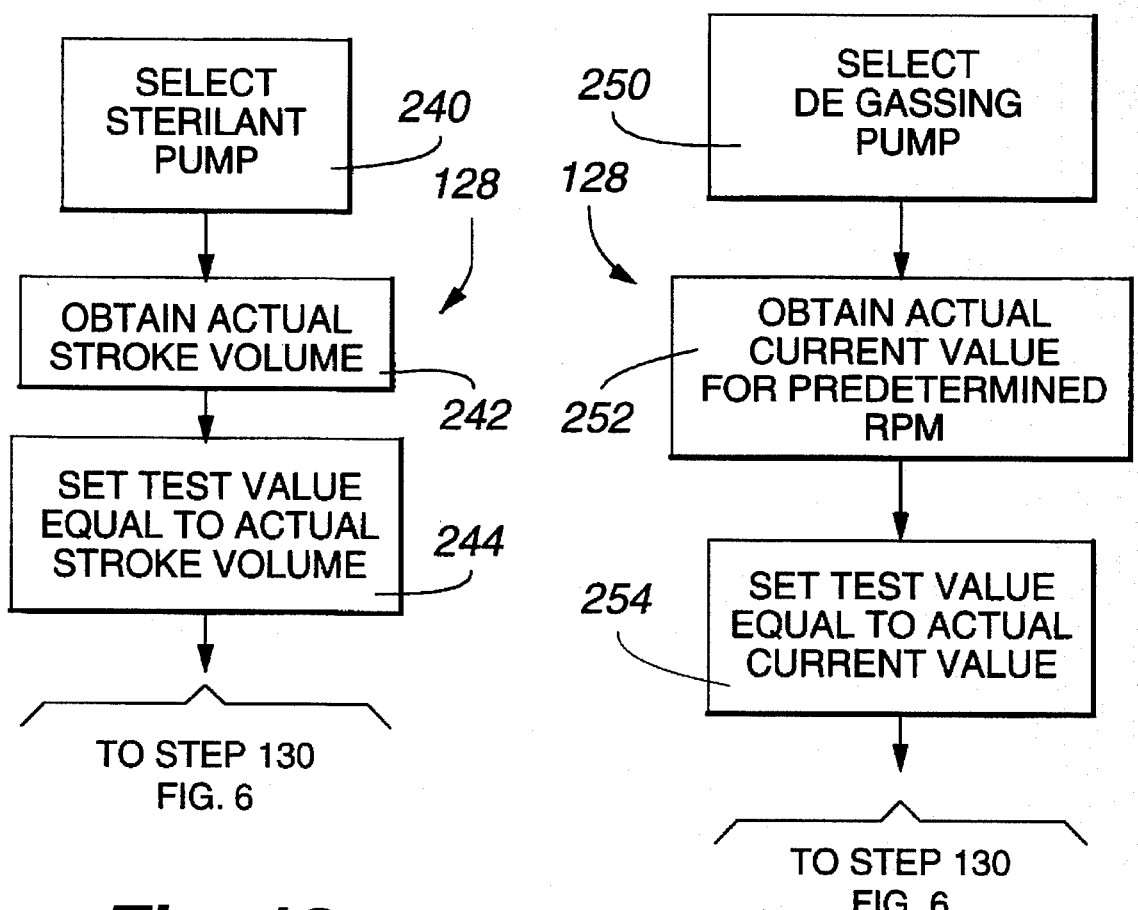
FIG. 13 is a flow chart illustrating the actions shown in FIG. 6 of computing a test value for a sterilant pump in a hydraulics flow path shown in FIGS. 3 and 4.
FIG. 14 is a flow chart illustrating the actions shown in FIG. 6 of computing a test value for a degassing pump in a hydraulics flow path shown in FIGS. 3 and 4.

The computation 128 of a test value for a sterilant pump 226 (FIG. 4) is shown in greater detail in FIG. 13. The sterilant plump 226 is used to deliver a predetermined amount of sterilant from a supply 228 to the hydraulics flow path for cleaning and disinfecting the hydraulics flow path before the dialysis machine is used. It is important that the quantity of sterilant supplied by the sterilant pump 226 be accurately measured because the proper concentration is necessary to achieve adequate disinfection. The sterilant pump 226 is connected to the sterilant supply 228 by a three way valve 230. The source of sterilant 228 is also connected to the valve 230. A burette 232 is connected to the sterilant pump 226.

When it is desired to deliver sterilant to the hydraulics flow path, the valve 230 is operated to connect the sterilant pump 226 to the sterilant source 228. The sterilant pump 226 is preferably a peristaltic pump. The rotational movement of the rotor of the peristaltic pump results in moving a constant volume of fluid through the pump. This constant volume is referred to as a "stroke." Each stroke of the pump 226 withdraws a predetermined volume of sterilant from the source 228 which is transferred to the burette 232. The sterilant fills the burette to a level determined by an optical sensor 234 positioned adjacent to the burette 232. The signals from the optical sensor 234 represent the volume of sterilant in the burette which was created by a predetermined number of strokes of the sterilant pump 226. As the sterilant pump experiences wear, the stroke volume will vary, usually decreasing. The stroke volume is the parameter which is measured to perform the trend analysis on the sterilant pump 226.

The computation 128 of the test value for the sterilant pump begins with the sterilant pump being selected for the trend analysis at 240. The value of the stroke volume is obtained from the level to which the burette is filled with sterilant, as shown at 242. The test value is thereafter made equal to the stroke volume at 244. With the test value for the sterilant pump established, the program flow progresses to step 130 shown in FIG. 6.

The threshold established for the sterilant pump at step 120 (FIG. 5) is the predetermined desired stroke volume. If the test value established at step 244 (FIG. 13) is less than the threshold as determined at 130 (FIG. 6), the maintenance count value is incremented at 132 (FIG. 6). The threshold established could also be a range of stroke volumes which are acceptable, in the case where a malfunctioning or failing sterilant pump could be revealed by a larger than desired stroke volume or a smaller than desired stroke volume.

The computation 128 of a test value for the degassing pump 162 (FIG. 4) is shown in greater detail in FIG. 14. The degassing pump 162 is used in conjunction with the heater 112 to recirculate fluid around the heater 112. The degassing pump 162 is used during dialysis treatments to remove any air which may have entered the hydraulics flow path.

The degassing pump 162 is typically driven by a direct current motor. The speed or rpm of the degassing pump motor is directly related to the quantity of current supplied to the motor. During operation, a predetermined rpm of the degassing pump motor establishes the desired pressure within the flow path through the heater 112. The amount of current to establish this desired rpm is read and is used as the parameter by which to analyze the trend characteristics of the degassing pump.

The degassing pump is selected for trend analysis at 250 in FIG. 14. When the degassing pump has reached the desired speed or rpm, the actual value or quantity of current required to drive the pump at that desired rpm is read at 252. The test value is then set equal to the actual current value at 254. The test value established at 254 is then employed in the program flow at step 130 shown in FIG. 6.

The threshold established at 120 (FIG. 5) for the degassing pump is a range of acceptable values for the current required to drive the degassing pump at the predetermined rpm. If the test value falls outside of the range of the threshold, as determined at 130 (FIG. 6), an abnormal event is indicated and the maintenance count value is incremented at 132 (FIG. 6).

Although a number of components of a dialysis machine have been discussed as susceptible for trend analysis, other components could also be evaluated using the present invention. Similarly, parameters other than those discussed above could be selected by which to evaluate the performance of the component under analysis. In general, a suitable parameter will be one which is supplied to the component and to which the component responds by delivering the intended performance or functionality. The present invention may be practiced adequately using any parameters of this nature on any component within the dialysis machine.

Use of the present invention with dialysis machines offers the capability of reducing maintenance costs associated with the machines. Components which are likely to fail may be replaced or serviced at regularly scheduled maintenance intervals, rather than at special or emergency maintenance calls. Multiple components may be replaced at one time if the trend analysis indicates that failure is imminent, rather than encountering the necessity for separate special service calls as each component fails at a different time. By predicting the expected date of failure or malfunction the regular service schedules can be adjusted to avoid unexpected failures. Dialysis machines in dialysis clinics may be maintained in a manner which avoids downtime during the period of the day when patients normally receive treatment. As a result, the costs of operating the dialysis equipment may be reduced or the rate of increase may be reduced. Many other significant improvements will be recognized after the present invention is fully appreciated.

A presently preferred embodiment of the invention and many of its improvements have been described with a degree of particularity. This description is a preferred example for implementing the invention, and is not necessarily intended to limit the scope of the present invention.

The invention claimed is:

1. A method of analyzing wear on at least one component in a dialysis machine, comprising the steps of:

establishing a threshold value which defines the limits of normal performance for each component to be analyzed;

monitoring actual performance of each component during use of the dialysis machine;

determining a test value from the actual performance monitored;

comparing the test value to the threshold value;

incrementing a maintenance count value in relation to each instance of the test value exceeding the threshold value; and analyzing the wear on the component by referring to the maintenance count value.

2. A method as defined in claim 1 further comprising the step of:

incrementing the maintenance count value each time the test value exceeds the threshold value.

3. A method as defined in claim 1 further comprising the steps of:

updating the maintenance count value with each instance of the test value exceeding the threshold value;

storing the updated maintenance count value;

incrementing the updated maintenance count value with each subsequent instance of the test value exceeding the threshold value; and resetting the maintenance count value after replacing or servicing the component under analysis.

4. A method as defined in claim 1 further comprising the steps of:

registering an abnormal event each time the test value exceeds the threshold value; and recording temporal information in association with each abnormal event.

5. A method as defined in claim 4 further comprising the steps of:

projecting trend information describing abnormal events for the component by use of the maintenance count values and the temporal information.

6. A method as defined in claim 5 further comprising the steps of:
obtaining expected life time or maintenance interval information for each component; and
predicting a failure or maintenance date for the component using the trend information and the life time or maintenance information.

7. A method as defined in claim 1 further comprising the steps of:
obtaining an actual performance value for the component by monitoring the actual performance of the component; and
determining the test value by equating the test value with the actual performance value.

8. A method as defined in claim 1 wherein the component is a peristaltic pump, and said method further comprises the steps of:
measuring a stroke volume of the peristaltic pump; and
directly relating the test value to the measured stroke volume.

9. A method as defined in claim 1 wherein the component is an electrical motor having a rotational rate which is directly related to the value of one of a voltage or current supplied to the motor, and said method further comprises the steps of:
measuring an actual value of the one of the voltage or current supplied to the electrical motor to achieve a predetermined rotational rate; and
directly relating the test value to the measured actual value of the one of the current or voltage.

10. A method as defined in claim 1 further comprising the steps of:
obtaining an actual performance value for the component by monitoring the actual performance of the component;
obtaining an ideal value related to the performance of the component; and
determining the test value by performing a mathematical calculation using the ideal value and the actual performance value.

11. A method as defined in claim 10 wherein the mathematical calculation is a subtraction.

12. A method as defined in claim 1 wherein the dialysis machine performs ultrafiltration dialysis treatment at a desired ultrafiltration rate, and the component is an ultrafiltration pump which has a feedback value related to the ultrafiltration rate, said method further comprising the steps of:
measuring an actual feedback value adjusted during the performance of the ultrafiltration dialysis treatment to obtain the desired ultrafiltration rate; and
determining the test value by subtracting a predetermined constant from the actual feedback value.

13. A method as defined in claim 1 wherein two components are analyzed and those components are a first and a second gear pump and each gear pump is driven by a separate motor energized on a duty cycle basis, said method further comprising the steps of:
measuring an actual on time of the duty cycle energizing the motor driving the first pump to produce a pressure from the first pump;
measuring an actual on time of the duty cycle energizing the motor driving the second pump to produce a pressure from the second pump, said measuring occurring when the pressure from the second pump is the same as the pressure from the first pump; and
determining the test value by calculating a ratio of the measured on times of the first and second pumps.

14. A method as defined in claim 13 further comprising the step of:
subtracting a constant value from the ratio of the measured on times.

15. A method as defined in claim 1 wherein two components are analyzed and those components are a first and a second flow meter, said method further comprising the steps of:
measuring an indicated flow rate of the first flow meter;
measuring an indicated flow rate of the second flow meter when the actual flow through the first and second flow meters is the same; and
determining the test value by calculating a taration constant equal to a ratio of the indicated flow rates of the first and second flow meters.

16. A method as defined in claim 15 further comprising the step of:
subtracting a constant value from the taration constant.

17. A method as defined in claim 1 wherein the component is a pump driven by a motor energized on a duty cycle basis, said method further comprising the steps of:
measuring an actual on time of the duty cycle energizing the motor under predetermined operating conditions of the pump;
obtaining an ideal value for the on time of the duty cycle energizing the motor under ideal predetermined operating conditions of the pump; and
obtaining the test value by determining the difference between the actual on time and the ideal value for the on time.

18. A method as defined in claim 1 wherein the dialysis machine includes a safety and control system using a processor device having a memory, and said method further comprises the step of:
performing the steps of determining the test value, comparing the test and threshold values and incrementing the maintenance count value by operations of the processor device.

19. A method as defined in claim 18 further comprising the steps of:
recording the values in the memory of the processor device.

20. A dialysis machine including a plurality of components used to perform dialysis treatments and a safety and control system having a processor device using memory by which to control the components to perform the dialysis treatments and by which to develop information for analyzing wear on at least one of the components, comprising:
means for monitoring actual performance of each component to be analyzed during use of the dialysis machine;
means for determining a test value from the actual performance monitored;
means for recording a threshold value which defines the limits of normal performance for each component to be analyzed;
means for comparing the test value to the threshold value to obtain a maintenance count value based on the comparison;

means for recording the maintenance count value in memory;

means for incrementing the maintenance count value in the memory in relation to each instance of the test value exceeding the threshold value; and means for selectively displaying the maintenance count value.

21. A dialysis machine as defined in claim 20 further comprising means for resetting the maintenance count value after replacing or servicing the component under analysis.

22. A dialysis machine as defined in claim 20 further comprising:

means for registering an abnormal event each time the test value exceeds the threshold value; and means for recording temporal information in association with each abnormal event.

23. A dialysis machine as defined in claim 22 further comprising means for projecting trend information describing abnormal events for the component by use of the maintenance count values and the temporal information.

24. A dialysis machine as defined in claim 20 wherein the component is a peristaltic pump, and said dialysis machine further comprises:

means for measuring a stroke volume of the peristaltic pump; and means for directly relating the test value to the stroke volume.

25. A dialysis machine as defined in claim 20 wherein the component is an electrical motor having a rotational rate which is directly related to the value of one of a voltage or current supplied to the motor, and said dialysis machine further comprises:

means for measuring an actual value of the one of the voltage or current supplied to the electrical motor to achieve a predetermined rotational rate; and means for directly relating the test value to the measured actual value of the one of the voltage or current.

26. A dialysis machine as defined in claim 20 wherein the dialysis machine performs ultrafiltration dialysis treatment at a desired ultrafiltration rate, and the component to be analyzed is an ultrafiltration pump which has a feedback value related to the ultrafiltration rate, said dialysis machine further comprising:

means for measuring an actual feedback value adjusted during the performance of the ultrafiltration dialysis treatment to obtain the desired ultrafiltration rate; and means for determining the test value by subtracting a predetermined constant from the actual feedback value.

27. A dialysis machine as defined in claim 20 wherein two components to be analyzed are a first and a second gear pump and each gear pump is driven by a separate motor energized on a duty cycle basis, said dialysis machine further comprising:

means for measuring an actual on time of the duty cycle energizing the first pump producing a pressure on the first pump;

means for measuring an actual on time of the duty cycle energizing the second pump producing a pressure on the second pump, said measuring occurring when the pressure on the first pump is the same as the pressure on the second pump; and means for determining the test value by calculating a ratio of the measured on times of the first and second pumps.

28. A dialysis machine as defined in claim 20 wherein two components to be analyzed are a first and a second flow meter, said dialysis machine further comprising:

means for measuring an indicated flow rate of the first flow meter;

means for measuring an indicated flow rate of the second flow meter when the actual flow through the first and second flow meters is the same; and means for determining the test value by calculating a taration constant equal to a ratio of the indicated flow rates of the first and second flow meters.

29. A dialysis machine as defined in claim 20 wherein the component is a pump driven by a motor energized on a duty cycle basis, said dialysis machine further comprising:

means for measuring an actual on time of the duty cycle energizing the motor under predetermined operating conditions of the pump;

means for calculating an ideal value for the on time of the duty cycle energizing the motor under ideal predetermined operating conditions of the pump; and means for obtaining the test value by determining the difference between the actual on time and the ideal value for the on time.

* * * * *